US011648101B2

(12) United States Patent
Pine

(10) Patent No.: US 11,648,101 B2
(45) Date of Patent: May 16, 2023

(54) REPOSITIONABLE SURGICAL ANCHORS

(71) Applicant: Davol Inc., Warwick, RI (US)

(72) Inventor: Thomas Pine, Warren, RI (US)

(73) Assignee: Davol Inc., Warwick, RI (US)

( * ) Notice: Subject to any disclaimer, the term of this patent is extended or adjusted under 35 U.S.C. 154(b) by 22 days.

(21) Appl. No.: 17/245,783

(22) Filed: Apr. 30, 2021

(65) Prior Publication Data

US 2022/0346927 A1    Nov. 3, 2022

(51) Int. Cl.
*A61F 2/00*    (2006.01)

(52) U.S. Cl.
CPC .... *A61F 2/0063* (2013.01); *A61F 2220/0016* (2013.01)

(58) Field of Classification Search
CPC ...... A61F 2220/0016; A61F 2220/0072; A61F 2/0063; A61B 17/08; A61B 17/0401; A61B 17/0057; A61B 17/064; A61B 17/068; A61B 17/0466; A61B 2017/00663; A61B 2017/00632; A61B 2017/00867
See application file for complete search history.

(56) References Cited

U.S. PATENT DOCUMENTS

| | | | | |
|---|---|---|---|---|
| 8,579,920 B2* | 11/2013 | Nering | ............... | A61B 17/0682 606/151 |
| 2002/0169465 A1* | 11/2002 | Bowman | ............ | A61B 17/0401 606/151 |
| 2009/0118734 A1* | 5/2009 | Bhatnagar | .......... | A61B 17/0642 606/75 |
| 2011/0071578 A1* | 3/2011 | Colesanti | ............. | A61B 17/064 606/305 |
| 2012/0179086 A1 | 7/2012 | Shank et al. | | |
| 2016/0143637 A1 | 5/2016 | Nering et al. | | |
| 2016/0317151 A1 | 11/2016 | Gupta et al. | | |
| 2017/0290577 A1 | 10/2017 | Sholev et al. | | |

OTHER PUBLICATIONS

International Search Report and Written Opinion, dated Jun. 2, 2022 for International Application No. PCT/US2022/020341.

* cited by examiner

*Primary Examiner* — Erich G Herbermann
(74) *Attorney, Agent, or Firm* — Wolf, Greenfield & Sacks, P.C.

(57) ABSTRACT

Embodiments related to surgical anchors are described. In some embodiments, a surgical anchor may include a selectively removable blocker which may prevent one or more barbs of the surgical anchor from engaging with adjacent tissue until the selectively removable blocker is removed.

17 Claims, 7 Drawing Sheets

REPOSITIONABLE SURGICAL ANCHORS

FIELD

Disclosed embodiments relate to repositionable surgical anchors.

BACKGROUND

A tissue defect, such as a hernia, is commonly repaired with an implantable prosthesis that is configured to cover and/or fill the defect. For some procedures, an implantable repair patch, such as a mesh patch, is sutured, stapled, tacked, or otherwise provisionally anchored in place over, under, or within the defect. Tissue integration with the patch, such as tissue ingrowth into and/or along the mesh fabric, may then eventually complete the repair.

Various repair patches are used for repairing soft tissue and muscle wall defects. Such patches are typically fabricated from polypropylene monofilaments that are knitted into a mesh having pores or interstices that promote tissue ingrowth and integration with the path. Such patches may be adapted to be fixed to tissue using attachment methods including sutures, staples, and/or tacks after the patch is positioned in a desired orientation to fix the patch in place.

BRIEF SUMMARY

According to one aspect, an implantable prosthesis for repairing a defect in a tissue includes an implantable patch body and at least one surgical anchor attached to the patch body, wherein at least one surgical anchor includes a head, a shaft extending distally from the head, wherein the shaft includes a pointed distal tip configured to pierce tissue, one or more barbs disposed on the shaft, a slot extending from a proximal surface to at least a distal surface of the head, and a blocker configured to be received in and selectively removed from the slot, wherein the blocker is configured to shield the one or more barbs from engaging adjacent tissue when the blocker is positioned in the slot.

According to another aspect, a surgical anchor for fixing a prosthetic to a tissue includes a head, a shaft extending distally from the head, wherein the shaft includes a pointed distal tip configured to pierce tissue, one or more barbs disposed on the shaft, a slot extending from a proximal surface to at least a distal surface of the head, and a blocker configured to be received in and selectively removed from the slot, wherein the blocker is configured to shield the one or more barbs from engaging adjacent tissue when the blocker is positioned in the slot.

According to yet another aspect, a method of implanting an implantable prosthesis for repairing a defect in a tissue includes inserting a surgical anchor into the tissue, removing a blocker disposed in a slot formed in the surgical anchor to expose one or more barbs of the surgical anchor, and engaging the one or more barbs with adjacent tissue.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION

Figure 1:
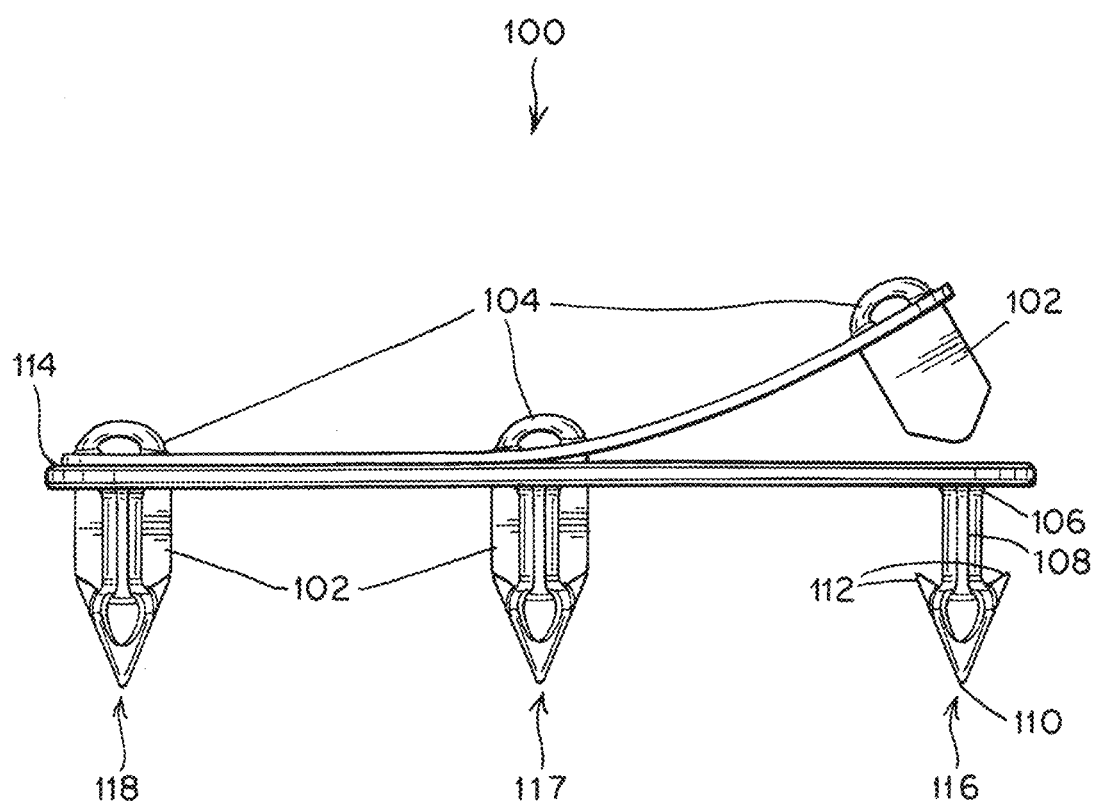
FIG. 1 is a front view of a set of repositionable anchors according to one illustrative embodiment.
Figure 2A:
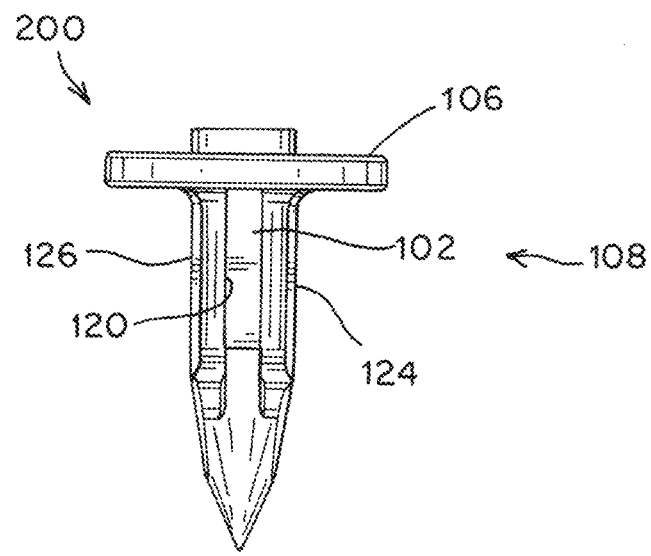
FIG. 2A is a side view of a repositionable anchor with a blocker inserted according to one illustrative embodiment.
Figure 2B:
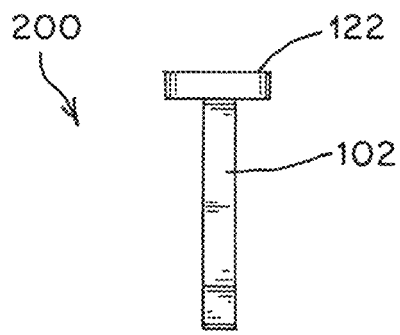
FIG. 2B is a side view of the repositionable anchor with the blocker removed according to the embodiment of FIG. 2A.
Figure 2B:
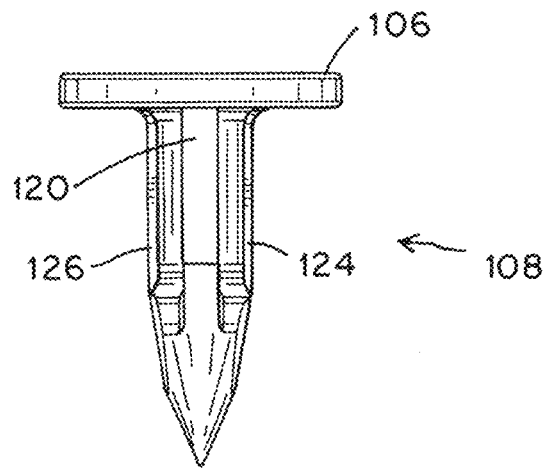
Figure 3A:
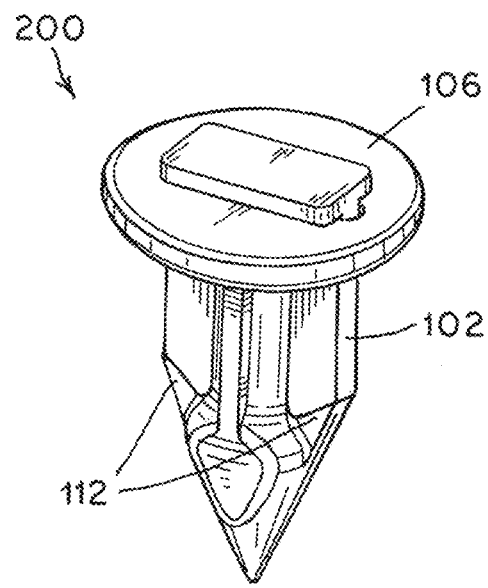
FIG. 3A is a perspective view of a repositionable anchor with a blocker inserted according to one illustrative embodiment.
Figure 3B:
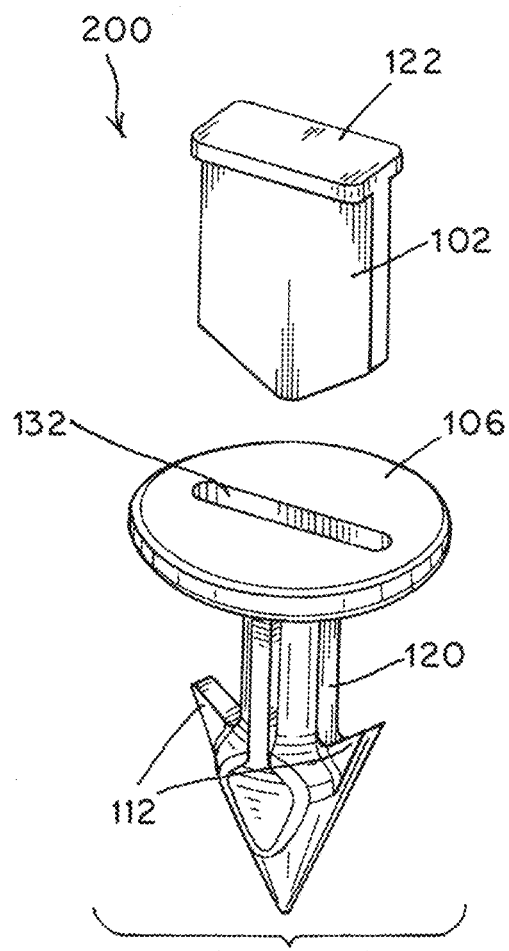
FIG. 3B is a side view of the repositionable anchor with the blocker removed according to the embodiment of FIG. 3A.

To repair a soft tissue defect in a patient, such as a hernia, a clinician may employ a surgically implantable prosthesis, such as a patch. In some instances, the clinician may implant the patch (e.g., a fabric mesh) by first positioning the patch in a desired orientation and then subsequently fixing the patch to the tissue defect by suturing, stapling, tacking, or otherwise fixing the patch to the tissue defect. Generally speaking, this results in the clinician using separate features and/or devices to position and orient a repair patch and subsequently fixating the patch to repair the tissue defect, increasing the complexity of a tissue repair surgery. For example, a clinician may first provisionally position the patch in a desired orientation. Then the clinician may provisionally suture, staple, or tack the patch to the tissue defect. The clinician may then confirm whether the patch is fixed in the appropriate orientation. If the patch is not in an appropriate orientation, the clinician may need to remove the suture(s), staple(s), and/or tack(s). Notably, removing the suture(s), staple(s), and/or tack(s) may result in the suture(s), staple(s), and/or tack(s) being rendered inoperable. The clinician may then reposition the patch and refix the patch to the tissue defect using additional suture(s), staple(s), and/or tack(s). This may result in increased post-operative pain for a patient, as well as wasted materials and an unwanted increase in overall surgical procedure time.

In view of the above, the inventor has recognized the advantages associated with surgical anchors that may transition between a first configuration that may be selectively inserted into and removed from tissue and a second configuration where the surgical anchors are retained in the associated tissue. Thus, a clinician may provisionally fix the patch to a tissue defect to confirm that a desired orientation has been achieved before fixing the patch for longer term implantation.

In some embodiments, a surgical anchor may include a selectively removable blocker that is configured to transition the anchor from a first configuration where the anchor may be removed from tissue and a second configuration where the anchor may be retained in the tissue. For example, in one embodiment, a blocker may be configured such that one or more portions of the anchor are unable to be fixedly engaged with the tissue when the blocker is inserted into a slot of the surgical anchor. Particularly, when the blocker is inserted into the slot of the surgical anchor, the blocker may shield one or more barbs of the surgical anchor from engaging with the tissue. Also, the surgical anchor may include a pointed distal tip capable of piercing tissue. Thus, when the surgical anchor with the blocker engaged is inserted into adjacent tissue, the clinician may removably pierce the tissue (e.g., to manipulate a patch into a desired orientation), while maintaining the ability to remove the surgical anchor from the tissue and re-pierce the tissue in a different location, if it is desired to reposition the associated patch body, or other prosthetic, and/or the surgical anchor itself. When the clinician needs to fixedly attach the surgical anchor to the tissue, the clinician may selectively remove the blocker, exposing the one or more barbs of the surgical anchor, thus allowing the one or more barbs to engage with the tissue.

In some embodiments, a surgical anchor may include a slot to accommodate a blocker until the blocker is removed by the clinician. For example, a surgical anchor may include a head and a shaft extending distally from the head. The slot may extend from a proximal surface of the head to at least an opposing surface of the head to permit the blocker to extend through the head when positioned in the anchor. In some embodiments, the slot may also extend through at least a portion of the shaft. One or more barbs and a distal pointed tip configured to pierce tissue may be located on a distal portion of the shaft. Thus, at least a portion of the blocker may shield the one or more barbs such that the one or more barbs are prevented from fixedly engaging with adjacent tissue when the blocker is positioned in the slot. In some embodiments, the slot may be formed between two opposing portions of the shaft, a side portion of the shaft, and/or the slot may not be formed in the shaft at all. Accordingly, the clinician may selectively remove the blocker from the slot via an opening of the slot formed in the head to expose the one or more barbs, allowing the surgical anchor to fixedly engage with adjacent tissue.

In some embodiments, an implantable prosthesis according to the present disclosure may include an implantable patch body and at least one surgical anchor as disclosed herein operatively connected to the patch body. Such an arrangement may allow a clinician to selectively remove and reposition the one or more anchors and associated prosthetic until a desired orientation and/or position is achieved. A device may include any appropriate number of anchors connected to a prosthetic. Additionally, the surgical anchors may be connected to a patch body, or other portion, of a prosthetic using sutures, welds, adhesives, and/or any other appropriate attachment method.

In some instances, it may be desirable for a plurality of surgical anchors affixed to a patch body to include features that allow a clinician to easily deploy the plurality of surgical anchors into a region of tissue. For example, in some embodiments, a prosthesis may include multiple surgical anchors pre-fixed to a patch body. In such embodiments, the prosthesis may include features to provide a rigid backing to one or more of the surgical anchors of the prosthesis. The rigid backing may serve to space each anchor of the plurality of anchors a predetermined distance apart and to support fixation of the patch body to the underlying tissue. Of course, the surgical anchors need not be pre-fixed to the patch body, as the surgical anchors may be added during implantation by the clinician. Additionally, other suitable combinations of pre-fixed anchors and anchors fixed to the patch body during implantation may be employed, depending on the application.

In embodiments where a prosthesis with multiple anchors is used, a plurality of rigid backings may be associated with different groups of the plurality of surgical anchors located in different regions of the patch body. For example, in some embodiments, the plurality of surgical anchors may be grouped into two or more groups extending around a periphery of the patch body. In some embodiments, the surgical anchors may be formed with, or connected to, the rigid backing (e.g., via molding or welding), though this need not be the case as the rigid backing may be attached to the surgical anchors via a press fit, a snap fit, or in any other appropriate manner.

In instances where multiple surgical anchors are used, including when multiple anchors are incorporated using backings, the plurality of surgical anchors may include a plurality of blockers (e.g., one blocker for each surgical anchor). In some embodiments, two or more of the plurality of blockers may be interconnected to facilitate removal of the interlinked blockers. For example, in such embodiments, a clinician may remove a plurality of interconnected blockers by pulling on an interconnecting structure and/or a blocker connected to the other interconnected blockers until each of the interconnected blockers are removed from the respective surgical anchors. In some embodiments, one or more of the plurality of blockers may include a loop or tab such that the clinician may pull on the loop or tab to remove the blockers. Alternatively or additionally, an individual blocker may also include such a loop or tab, depending on the application. In either case, the clinician may pull on the structure using one or more appendages (e.g., a thumb and forefinger), one or more tools (e.g., a pair of forceps), and/or a robotic surgical system. Thus, a clinician may remove multiple blockers in a single motion or step.

The features described above related to grouping the surgical anchors with a rigid backing and interconnecting the blockers may be employed either in conjunction with one another or separately, depending on the application.

An implantable prosthesis according to the present disclosure may be suitable for mending an anatomical defect, and may be particularly suitable for mending defects in, and weaknesses of, soft tissue and muscle walls or other anatomical regions. The phrase "mending a defect" may include acts of repairing, augmenting, and/or reconstructing a defect and/or a potential defect. For ease of understanding, and without limiting the scope of the disclosure, the prosthesis is described below particularly in connection with mending a hernia including, but not limited to, one or more of an indirect inguinal hernia, a direct inguinal hernia, a femoral hernia, ventral hernias and/or other weakness or rupture of the abdominal tissue. It should be understood, however, that the prosthesis is not so limited and may be employed in other anatomical procedures, as should be apparent to one of skill in the art. For example, and without limitation, the prosthesis may be employed for chest or abdominal wall reconstruction, or large defects, such as those that may occur in obese patients. The prosthesis may include one or more features, each independently or in combination, contributing to such attributes.

In addition to the above, a prosthesis according to the present disclosure may include a repair fabric having a body portion that is configured to cover or extend across a defect opening or weakness when the body portion is placed against the defect. The repair fabric may be in the form of a patch (as described above), although the prosthesis may employ other configurations as should be apparent to one of skill in the art. The patch may have a planar or non-planar configuration suitable for a particular procedure employed for mending a defect.

The prosthesis may be used for mending tissue defects using various surgical techniques, including open, laparoscopic, hybrid (e.g., Kugel procedure), and robotic techniques. During open procedures, the prosthesis may be placed through a relatively large incision made in the abdominal wall and layers of tissue and then the defect is filled or covered with the repair fabric. During laparoscopic and hybrid procedures, the prosthesis may be collapsed, such as by rolling or folding, into a reduced configuration for entry into a subject, either directly through a comparatively smaller incision or through a slender laparoscopic cannula that is placed through the incision. The prosthesis may have a particular application with robotic procedures in which placement of the prosthesis is achieved using surgical robotic tools which may involve passage of the prosthesis through a relatively small cannula (e.g., 8 mm) as compared to a cannula (e.g., 10-12 mm) typically employed for more conventional laparoscopic techniques.

The surgical anchors described herein may be made of any suitable material. For example, in some instances, the surgical anchors may be made of a rigid plastic, such as Polyethylene, high density Polyethylene, Polylactic Acid, metals (e.g., stainless steel, titanium, magnesium alloys, and/or other appropriate metals), or any other suitable material. In some instances, the surgical anchors may be made of a biocompatible material. Alternatively or additionally, the surgical anchors may be formed from a bioresorbable material. Of course, the surgical anchors may be made of any appropriate material depending on the application. Further, in some embodiments, the blockers of a surgical anchor may be made from a bioresorbable material.

The patch body described herein may be made of any suitable material including woven, non-woven, and membrane-based materials. For example, in some instances, the patch body may be a mesh, such as a Poly-4-hydroxybutyrate mesh. In some instances, the patch body may be made of a biocompatible material. Alternatively or additionally, the patch body may be formed from a bioresorbable material. In some embodiments, the patch body may include a barrier formed from one or more silicate materials. Of course, the patch body may be made of any appropriate material, depending on the application.

The surgical anchors may be attached to the patch body in any suitable manner. For example, the surgical anchors may be attached to the patch body using an adhesive, ultrasonic welding, thermal welding, sewing, or any other suitable manner of attachment. Of course, any appropriate manner of attaching the surgical anchors to the patch body may be employed, depending on the application.

In some embodiments, a surgical anchor may include an overall length, such as a maximum dimension along a longitudinal axis of the device, that is less than or equal to 0.375 in, 0.35 in, 0.325 in, and/or another appropriate length. Correspondingly, a surgical anchor may have an overall length greater than or equal to 0.125 in, 0.15 in, 0.175 in, and/or another appropriate length. Combinations of the above-noted ranges are contemplated, including, but not limited to, overall lengths between 0.125 in and 0.375 in, between 0.15 in and 0.35 in, and between 0.175 in and 0.325 in. In some embodiments, the overall length of a surgical anchor is 0.27 in. Of course, any suitable overall length may be employed, depending on the application.

In some embodiments, a surgical anchor may include an overall width, such as a maximum transverse dimension along a lateral axis of the anchor that is transverse to a longitudinal axis of the anchor, that is less than or equal to 0.188 in, 0.18 in, 0.163 in, and/or another appropriate width. Correspondingly, a surgical anchor may have an overall width greater than or equal to 0.062 in, 0.075 in, 0.088 in, and/or another appropriate width. Combinations of the above-noted ranges are contemplated, including, but not limited to, overall widths between 0.062 in and 0.188 in, between 0.075 in and 0.18 in, and between 0.088 in and 0.188 in. In some embodiments, the overall width of a surgical anchor is 0.135 in. Of course, any suitable overall width may be employed, depending on the application.

In some embodiments, a surgical anchor may include a minimum pull-out force, such as a minimum force that a single surgical anchor may withstand while remaining fixedly engaged with adjacent tissue, that is greater than or equal to 0.16 lbf, and/or another appropriate force. A range of the above-noted minimum pull-out force is contemplated, including, but not limited to, minimum pull-out forces between 0.08 lbf and 0.24 lbf. The range of the above-noted minimum pull-out forces may coincide with the range of dimensions also noted above (e.g., smaller anchor dimensions may equate to a smaller minimum pull-out force). Of course, any suitable pull-out force may be employed, depending on the application. Additionally, the noted pull-out forces may be measured using any appropriate method including, for example, a pullout force from a tissue analog high density synthetic foam substrate to replicate tissue properties as measured using an appropriate tensile tester.

In some embodiments, a prosthesis used with the disclosed surgical anchors is bioresorbable. For example, in some embodiments, the components of the prosthesis are formed from bioresorbable materials (e.g., as described above). Alternatively or additionally, the prosthesis may include a temporary resorbable adhesive applied to the patch body to help keep the patch body in place during implantation.

The features described above, alone or in conjunction with one another, may serve to provide benefits in certain applications in addition to permitting the anchors and an associated prosthetic to be easily repositioned. For example, the slots in the anchor may facilitate additional blood flow in a patient at the surgical site, thus leading to quicker recovery times. Particularly, the additional blood flow may allow for an increased rate of tissue in-growth at the surgical site. Further, since the blocker may shield the one or more barbs of the surgical anchor during implantation, the patch body may be more easily manipulated by the clinician. For example, the patch body may be rolled up for laparoscopic insertion, and the blockers may shield the barbs from snagging on the patch body. Alternatively or additionally, the ability for a clinician to manipulate the position of the surgical anchors before removing the blockers may allow for a better overall fit of the anchors relative to the tissue, resulting in a more uniform strong hold in multiple directions, and assisting a clinician in fixing the prosthesis in an approximately flat position against the tissue when completing the repair.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 illustrates one embodiment of a plurality of surgical anchors 100 configured to attach an implantable mesh, or other prosthetic, to tissue by engaging with adjacent tissue. The plurality of surgical anchors 100 includes three interconnected surgical anchors 116, 117, 118. The surgical anchor 116 comprises a head 106 and a shaft 108 extending distally away from the head (e.g., in a direction in which the fasteners are deployed during insertion into tissue). On a distal portion of the shaft 108, the shaft 108 includes a pointed distal tip 110 configured to pierce tissue and barbs 112. In some embodiments, the barbs may correspond to structures that extend outwards from the shaft in a radial direction. Additionally, in some embodiments, the one or more barbs may also extend at least partially in a proximately oriented direction such that the barbs extend at an angle from the shaft which may help to engage with tissue to retain the surgical anchors in a desired position once deployed. For example, such a configuration may allow the surgical anchor 116 to penetrate and fixedly engage with adjacent tissue where the pointed tip 110 is deployed into tissue causing the shaft 108 to penetrate and extend into the tissue. If the barbs are uncovered, as shaft 108 enters the tissue wall, barbs 112 engage the tissue wall, fixing the surgical anchor 116 in the tissue wall.

While the barbs may retain the one or more surgical anchors in a tissue once deployed, in some instances, it may be desirable for the barbs 112 not to engage with the tissue wall until a clinician desires to fixedly engage the surgical anchor with the tissue wall. Accordingly, the one or more surgical anchors 116 may include features to prevent the barbs 112 of the surgical anchor 116 from engaging with the tissue wall. Particularly, a surgical anchor 112 may include a selectively removable blocker 102. The blocker 102 may be configured to prevent the barbs 112 from engaging with the tissue wall when assembled with the surgical anchor, preventing the surgical anchor 116 from being fixedly engaged with the tissue wall. Thus, a clinician may penetrate the tissue wall with the pointed distal tip 110, remove the anchor from the tissue, and reposition the anchor until a desired position and/or orientation of the anchor relative to the tissue is achieved. For example, the clinician may turn the surgical anchor 116 when inserted into the tissue wall until the surgical anchor 116 is positioned in the desired orientation. Alternatively or additionally, after piercing the tissue wall, the clinician may choose to remove the surgical anchor 116 from the tissue wall and penetrate the tissue wall in a different location to achieve the desired position and/or orientation without destroying, damaging, or otherwise rendering the surgical anchor 116 inoperable. Once the clinician has achieved the desired position and/or orientation of the anchor relative to the tissue the anchor is deployed into, the clinician may remove the blocker 102, allowing the one or more barbs 112 of the surgical anchor to fixedly engage with the tissue wall.

A blocker 102 may achieve the above noted functionality by shielding the barbs 112, preventing the barbs 112 from engaging with the tissue wall. Particularly, in the illustrated embodiment, surgical anchors 117, 118 show the blocker 102 in the shielding configuration where the blockers extend radially outwards from the shaft up to a position at, or proximate to, an outer edge or point of an associated barb. In some embodiments, a shape of a distal surface of a blocker may compliment a profile of a proximal surface of a corresponding barb located adjacent to that portion of the blocker such that the blocker prevents the engagement of the barb with surrounding tissue when the blocker is disposed in a corresponding slot formed in the fastener. In contrast, the surgical fastener 116 is shown in the exposed configuration with the barbs 116 being exposed and prepared to engage with a tissue wall and blocker 102 removed from the surgical anchor 116. A clinician may remove the blocker 102 by pulling on a tab 104, or other appropriate structure. In some embodiments, and as shown in the figure, the blockers 102 of each of the surgical anchors 116, 117, 118 may be joined together by a flexible strip or other connecting structure. Accordingly, a clinician may remove multiple blockers 102 by pulling continuously on a single tab 104 or other portion of the joined fasteners. Thus, the clinician may remove all of the blockers 102 in a single motion or step.

It should be appreciated that in the illustrated embodiment, the surgical anchors 117, 118 are similarly configured to surgical anchor 116, though the surgical anchors 117, 118 may be configured different from one another and the surgical anchor 116, depending on the application. Of course, the surgical anchors 116, 117. 118 may be configured in any appropriate manner.

Though the embodiments illustrated in the figures show surgical anchors with two barbs 112, it should be appreciated that this need not be the case. For example, configurations with one, three or four or more barbs are also contemplated. Additionally, the barbs may be configured in any suitable configuration. For example, the barbs 112 as illustrated are shown on opposing sides of the shaft 108. However, in embodiments with three barbs, the barbs may be in a triangular or other suitable configuration. In embodiments with four barbs, the barbs may be in a cruciform or other suitable configuration. Thus, it should be understood that any appropriate configuration and number of barbs may be employed, depending on the application.

While the above embodiment illustrates multiple fasteners integrated with a rigid backing, the use of individual surgical anchors is also contemplated. For example, a surgical anchor according to the present disclosure may be formed as a single surgical anchor 200, as shown in the embodiment of FIGS. 2A-3B. In the illustrated embodiment, the surgical anchor 200 includes a slot 120 extending from a proximal surface of the head, through the head to an opposing distal surface of the head, and through a portion of the shaft 108. In instances where the slot is formed at least partially in the shaft, the slot may be formed on and extend along at least a portion of the length of an outer portion of the shaft. Alternatively, a slot may be formed on and extend along at least a portion of a length of an inner portion of the shaft where a first portion 124 and a second portion 126 opposite from the first portion may form opposing surfaces that define a gap therebetween corresponding to the slot. However, embodiments in which the slot is not formed in the shaft are also contemplated. In either case, the slot may be sized and shaped to receive the blocker 102 in the slot. Regardless of the specific size and/or shape of a slot, the slot 120 may be sized and shaped to receive and hold the blocker 102 therein to block at least a portion of a proximal surface of the one or more barbs from engaging adjacent tissue prior to a clinician removing the blocker 102 from the surgical anchor 200.

As shown in FIGS. 2A-3B, the blocker 102 may be configured without the tab 104. In the embodiment of FIGS. 2A-3B, the blocker alternatively includes a blocker head 122, which a clinician may pull on to remove the blocker 102 from the slot 120. Additionally, in some embodiments, the blocker head 122 may also rest flush with the head 106 when the blocker 102 is engaged with the surgical anchor 200, reducing the risk that the blocker may be mistakenly disengaged from the slot 120. However, the structure and shape of a proximal portion of the blocker may correspond to any desired structure and/or shape that permits the blocker to be selectively removed from the surgical anchor during usage. Accordingly, it should be understood that the structure and shape of the blocker is not limited to only the specific structures shown in the figures as the disclosure is not limited in this fashion.

Surgical anchor 200 may also include one or more openings 132 formed in a proximal surface of the head 106. The one or more openings 132 may correspond to a proximal portion of the one or more slots and may be sized and shaped to allow a body of the blocker 102 to be inserted into the slot 120. The overall slot and/or blocker may also be configured to prevent the blocker from being inserted too far into the slot. For example, the blocker head 122 may be sized and shaped to prevent insertion into the slot as illustrated by the blocker head with a larger transverse dimension than the adjacent slot. Alternatively, the slot may simply have an overall size and/or shape that prevents the blocker from being inserted beyond a desired position through the use of corresponding mechanical interferences such as that present between a proximal surface of the one or more barbs and a distal surface of the blocker. In the illustrated embodiment, the center of the opening 132 is aligned at the center of the slot 120, shaft 120, and head. However, this need not be the case, as the opening, head, shaft, and slot may be configured in any suitable manner depending on the application.

In the above embodiment, the slot 120 is configured with a rectangular profile. However, in some embodiments, the one or more slots formed to receive one or more corresponding blockers may take on any suitable shape (e.g., to accommodate the blocker 102) including, but not limited to, square, triangular, ovular, and/or any other appropriate shape. Particularly, in some embodiments, the blocker 102 and the slot 120 may be configured with complementary shapes and/or sizes.

Figure 4A:
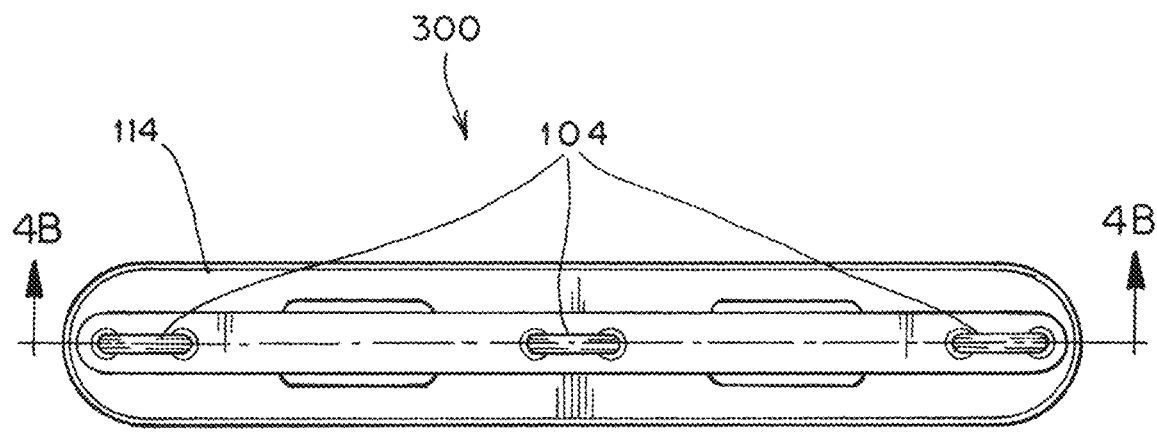
FIG. 4A is a top view of a set of repositionable anchors with a blocker inserted according to one illustrative embodiment.
Figure 4B:
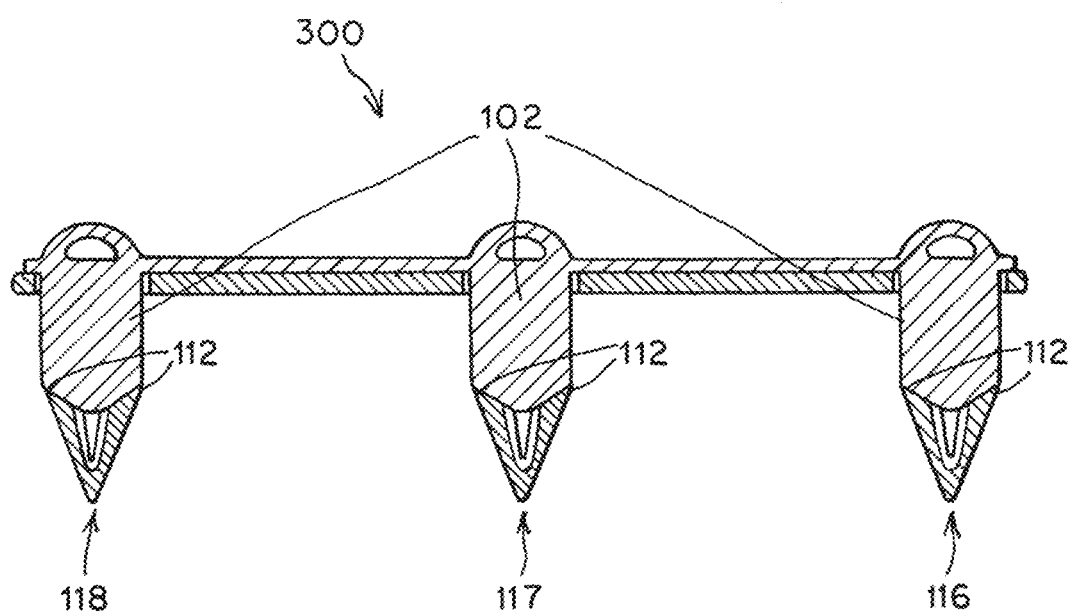
FIG. 4B is a cross sectional front view of the set of repositionable anchors with the blocker inserted according to the embodiment of FIG. 4A taken along line 4B-4B.
Figure 5A:
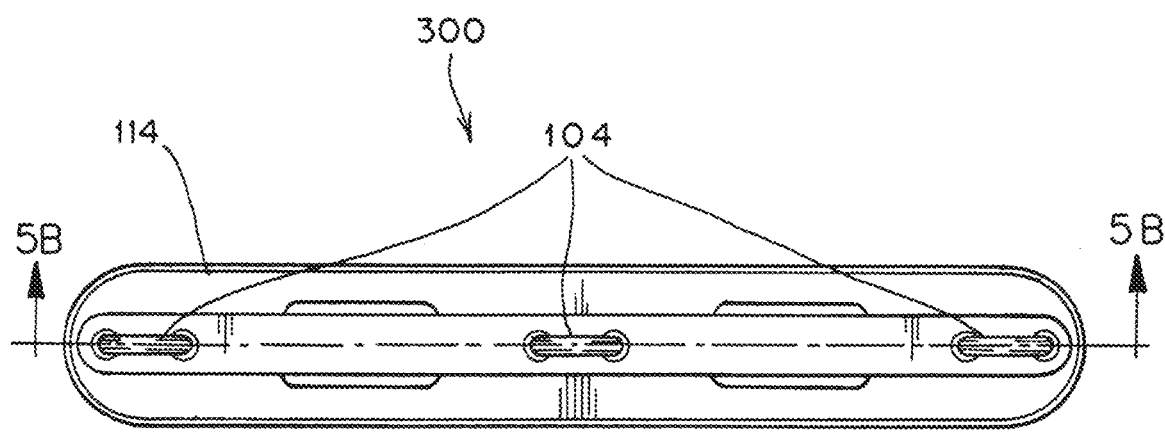
FIG. 5A is a top view of a set of repositionable anchors with a blocker removed according to one illustrative embodiment.
Figure 5B:
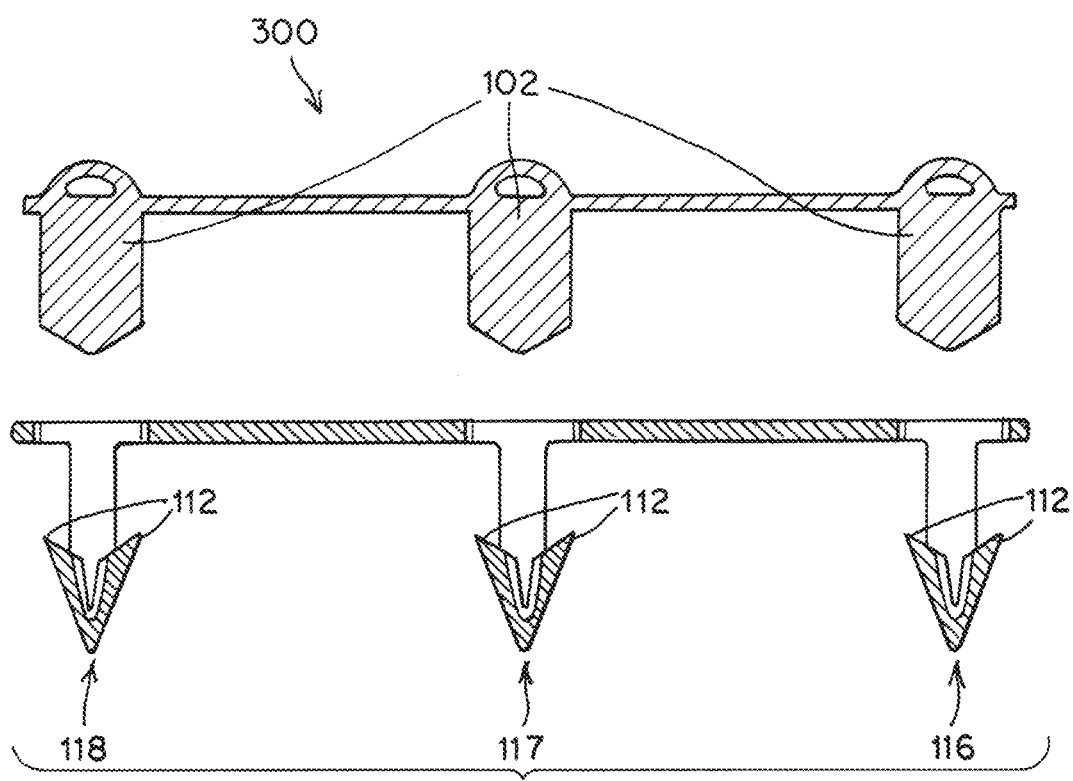
FIG. 5B is a cross sectional front view of the set of repositionable anchors with the blocker removed according to the embodiment of FIG. 5A taken along line 5B-5B.

FIGS. 4A-5B illustrate an embodiment of a plurality of surgical anchors 300 incorporated with a rigid backing 114 such that the surgical anchors may be deployed and unshielded together. In the illustrated embodiment, the plurality of surgical anchors 300 are interconnected via a rigid backing 114 which the surgical anchors may either be integrally formed with or connected to. The illustrated blockers 102 may be interconnected by an appropriate rigid or flexible strip, or other connecting structure similar to the embodiment of FIG. 1, or separate blockers that are separately removable may be used as well. FIGS. 4A-4B show the plurality of surgical anchors 300 in the shielded configuration, where the barbs 112 are prevented from fixedly engaging with adjacent tissue by the associated blocker of each anchor. In contrast, FIGS. 5A-5B show the plurality of surgical anchors 300 in an exposed configuration, where the blockers have been removed and the barbs 112 of each anchor are free to engage with adjacent tissue. In the illustrated embodiment, the blockers 102 are shaped to cover at least a proximal portion of barbs 112. In particular, in some embodiments, the blockers 102 extend outwards from the shaft, and in some embodiments radially outwards from the shaft such that the blocker extends up to, or past, a radial position an outermost portion of an associated barb. Thus, when blockers 102 are in the shielded configuration, the barbs 112 are prevented from engaging with adjacent tissue. Conversely, as shown in FIGS. 5A-5B, when the blockers 102 are removed from the plurality of surgical anchors 300, the barbs 112 are exposed and free to engage with adjacent tissue.

While plate shaped blockers 102 are shown in the figures, it should be understood that a blocker may take on any suitable shape. For example, in an alternative embodiment, the blockers may be generally u-shaped and configured to be received in slots formed in portions of the head located on opposing sides of the shaft such that the legs of the blocker extend along opposing portions of a solid shaft. Of course, the blockers 102 may take on any suitable shape, depending on the application.

Figure 6:
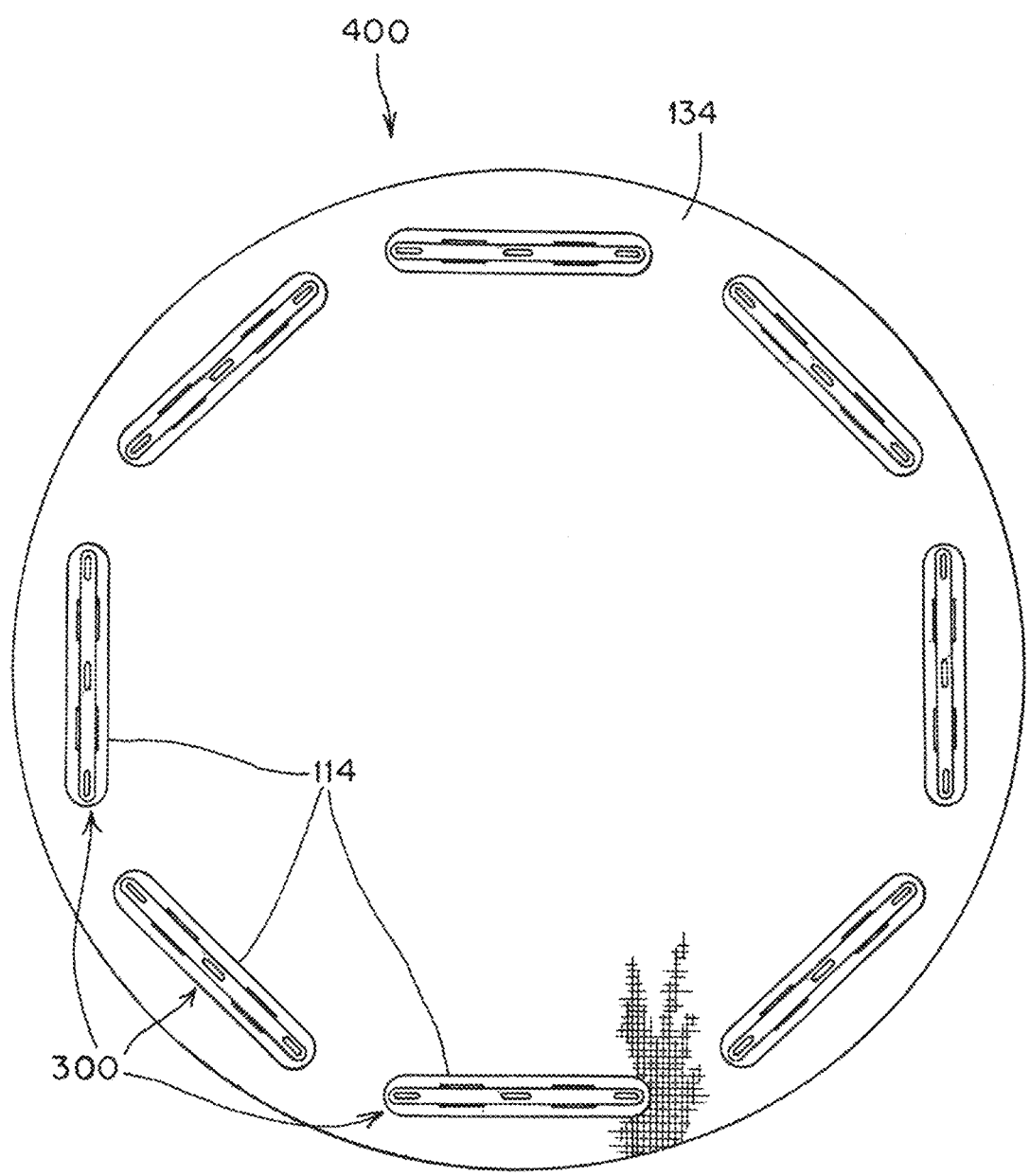
FIG. 6 is a top view of a prosthetic incorporating multiple sets of repositionable anchors according to one illustrative embodiment.

FIG. 6 illustrates an embodiment of an implantable prosthesis including a patch body 134 and multiple separate groups of surgical anchors 300 are pre-fixed to the patch body 134. In the illustrated embodiment, the pluralities of surgical anchors 300 are disposed around a periphery of the patch body. Particularly, the pluralities of surgical anchors 300 may be arranged on the patch body 134 in any suitable manner. In the illustrated embodiment, the separate groups of fasteners are incorporated into separate rigid backings 114 as described above. In such an embodiment, the clinician may grip a rigid backing 114 and push on the rigid backing 114 to implant one group of surgical anchors 300 into adjacent tissue. However, embodiments in which rigid backings are not used are also contemplated. Such an arrangement of an implantable prosthesis with surgical anchors preassembled there with may permit a clinician to more easily position and attach the prosthesis 400 to tissue.

Figure 7:
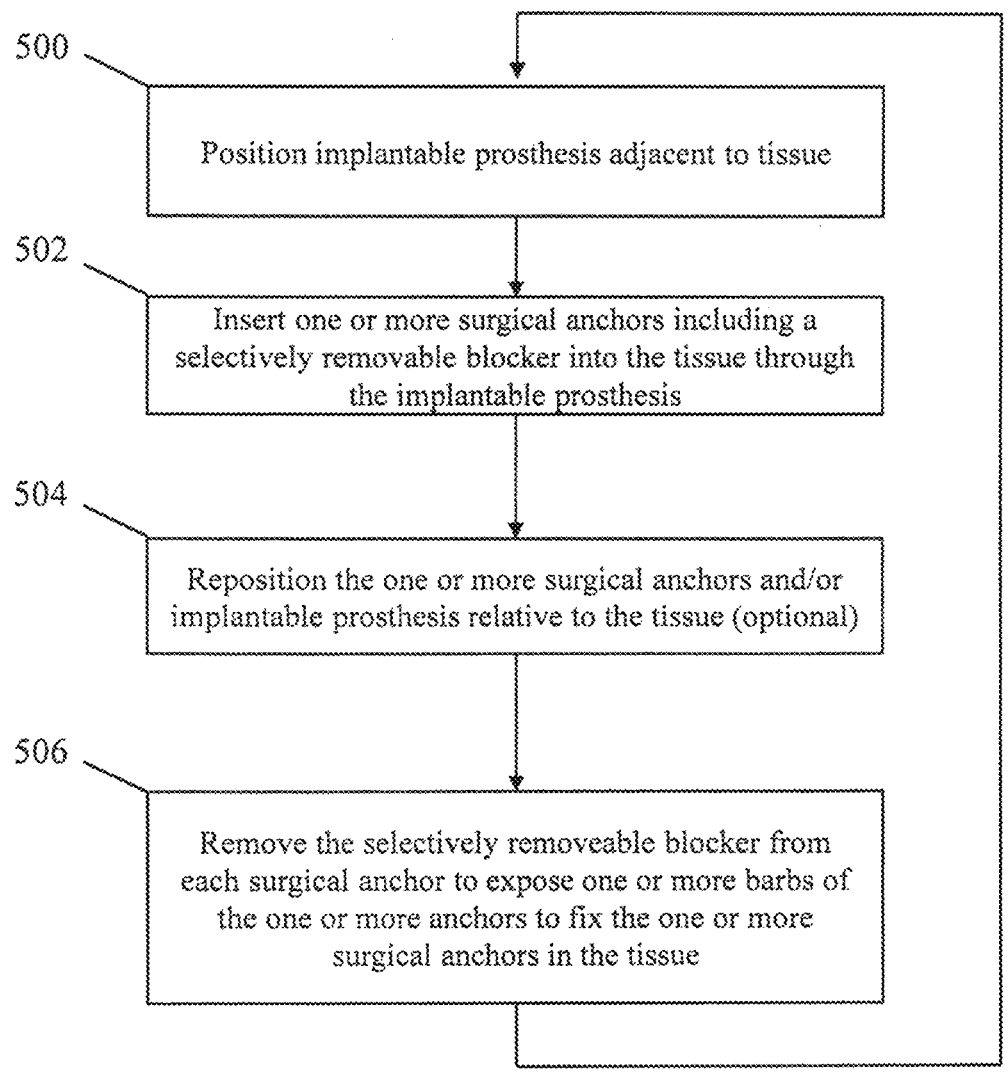
FIG. 7 is a flow chart illustrating a method of using a repositionable anchor according to one illustrative embodiment.

FIG. 7 is a flowchart illustrating an exemplary method for deploying a prosthesis including a patch body and at least one surgical anchor according to the present disclosure. In the illustrated method, at step 500, a clinician may position an implantable prosthesis (e.g., such as the implantable prostheses described above) adjacent to tissue. Then, at step 502, the clinician may insert one or more surgical anchors (e.g., the surgical anchors described above) into the tissue through the implantable prosthesis. At step 504, if a desired position and/or orientation of the anchor and/or prostatic is not already achieved, the clinician may reposition the one or more surgical anchors relative to the tissue. As described above, this may include removing any combination of the one or more surgical anchors from the tissue and re-inserting the same combination of the one or more surgical anchors into the tissue, for example, in a different location and/or orientation. At step 506, the clinician may then remove a blocker from each of the surgical anchors to expose one or more barbs of the surgical anchor which are configured to fixedly engage with the tissue, thus fixing the one or more surgical anchors to the tissue. Of course, any suitable method of deploying a prosthesis may be employed, depending on the application.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An implantable prosthesis for repairing a defect in a tissue, the prosthesis comprising:
   an implantable patch body; and
   at least one surgical anchor attached to the patch body, wherein the at least one surgical anchor comprises:
   a head;
   a shaft extending distally from the head, wherein the shaft includes a pointed distal tip configured to pierce tissue;
   one or more barbs disposed on the shaft;
   a slot extending from a proximal surface to at least a distal surface of the head; and
   a blocker configured to be received in and selectively removed from the slot, wherein the blocker is configured to shield the one or more barbs from engaging adjacent tissue when the blocker is positioned in the slot.

2. The implantable prosthesis of claim 1, wherein the slot is formed within at least a portion of the shaft.

3. The implantable prosthesis of claim 1, wherein the at least one surgical anchor is one of a plurality of surgical anchors.

4. The implantable prosthesis of claim 3, wherein at least two surgical anchors of the plurality of surgical anchors are connected by a rigid backing.

5. The implantable prosthesis of claim 3, wherein the at least two blockers are connected.

6. The implantable prosthesis of claim 3, wherein the plurality of surgical anchors are disposed around a perimeter of the patch body.

7. The implantable prosthesis of claim 1, wherein the blocker is sized and shaped such that when the blocker is fully inserted into the slot, the blocker is positioned against a proximal portion of the one or more barbs such that the blocker blocks the one or more barbs from engaging with adjacent tissue.

8. The implantable prosthesis of claim 1, wherein the slot includes an opening located on the proximal surface of the head configured to accommodate insertion of the blocker through the opening.

9. The implantable prosthesis of claim 1, wherein the surgical anchor and the implantable prosthesis are bioresorbable.

10. The implantable prosthesis of claim 1, wherein the surgical anchor and the implantable prosthesis are biocompatible.

11. The implantable prosthesis of claim 1, wherein the surgical anchor is configured to exhibit a pullout force of at least 0.16 lbf.

12. A surgical anchor for fixing a prosthetic to a tissue, the surgical anchor comprising:
   a head;
   a shaft extending distally from the head, wherein the shaft includes a pointed distal tip configured to pierce tissue;
   one or more barbs disposed on the shaft;
   a slot extending from a proximal surface to at least a distal surface of the head; and
   a blocker configured to be received in and selectively removed from the slot, wherein the blocker is configured to shield the one or more barbs from engaging adjacent tissue when the blocker is positioned in the slot.

13. The surgical anchor of claim 12, wherein the slot is formed within at least a portion of the shaft.

14. The surgical anchor of claim 12, wherein the blocker is sized and shaped such that when the blocker is fully inserted into the slot, the blocker is positioned against a proximal portion of the one or more barbs such that the blocker blocks the one or more barbs from engaging with adjacent tissue.

15. The surgical anchor of claim 12, wherein the slot includes an opening located on the proximal surface of the head configured to accommodate insertion of the blocker through the opening.

16. The surgical anchor of claim 12, wherein the surgical anchor is bioresorbable.

17. The surgical anchor of claim 12, wherein the surgical anchor is configured to exhibit a pullout force of at least 0.16 lbf.

* * * * *